(12) United States Patent
Gneuss

(10) Patent No.: US 8,256,271 B2
(45) Date of Patent: Sep. 4, 2012

(54) VISCOMETER FOR MOLTEN PLASTIC

(75) Inventor: Detlef Gneuss, Bad Oeynhausen (DE)

(73) Assignee: Gneuss Kunststofftechnik GmbH, Bad Oeynhausen (DE)

( * ) Notice: Subject to any disclaimer, the term of this patent is extended or adjusted under 35 U.S.C. 154(b) by 403 days.

(21) Appl. No.: 12/665,730

(22) PCT Filed: Jul. 16, 2008

(86) PCT No.: PCT/EP2008/005810
§ 371 (c)(1),
(2), (4) Date: Dec. 21, 2009

(87) PCT Pub. No.: WO2009/010281
PCT Pub. Date: Jan. 22, 2009

(65) Prior Publication Data
US 2010/0186486 A1    Jul. 29, 2010

(30) Foreign Application Priority Data
Jul. 19, 2007   (DE) .......................... 10 2007 033 969

(51) Int. Cl.
*G01N 11/08* (2006.01)
(52) U.S. Cl. ...................................... 73/54.09
(58) Field of Classification Search ................ 73/54.04, 73/54.09
See application file for complete search history.

(56) References Cited

U.S. PATENT DOCUMENTS

| | | | | |
|---|---|---|---|---|
| 4,587,837 A | | 5/1986 | Newbould | 73/56 |
| 4,817,416 A | * | 4/1989 | Blanch et al. | 73/54.04 |
| 5,076,096 A | * | 12/1991 | Blyler et al. | 73/54.09 |
| 5,347,852 A | * | 9/1994 | Mode | 73/54.04 |
| 5,652,376 A | | 7/1997 | Deleeuw et al. | 73/54.35 |
| 6,246,918 B1 | | 6/2001 | Wang et al. | 700/97 |
| 2004/0187565 A1 | * | 9/2004 | Sutton | 73/104 |

FOREIGN PATENT DOCUMENTS

| | | |
|---|---|---|
| DE | 8709717 | 12/1988 |
| GB | 2396429 | 6/2004 |
| JP | 2004069363 | 3/2004 |

* cited by examiner

Primary Examiner — Hezron E Williams
Assistant Examiner — Nathaniel Kolb
(74) Attorney, Agent, or Firm — Andrew Wilford

(57) ABSTRACT

A viscometer for molten plastic has a housing having first and second relatively displaceable parts with generally complementary and substantially planar faces. The first part is formed with a throughgoing melt passage adapted for connection in a flow system of the molten plastic. A hinge interconnects the parts. An outgoing conduit extends from the melt to a pump intake and from a pump output to an opening on the face of the first housing part. A plurality of sensors on one of the parts are connected to respective openings on the face of the one part. A return conduit extends from another opening on the face of the first housing part offset from the opening of the outgoing line. An exchangeable metal foil formed with a slot into which all of the openings open is engaged tightly between the two faces.

16 Claims, 1 Drawing Sheet

VISCOMETER FOR MOLTEN PLASTIC

CROSS REFERENCE TO RELATED APPLICATIONS

This application is the US-national stage of PCT application PCT/EP2008/005810, filed 16 Jul. 2008, published 22 Jan. 2009 as WO2009/010281, and claiming the priority of German patent application 102007033969.2 itself filed 19 Jul. 2007, whose entire disclosures are herewith incorporated by reference.

FIELD OF THE INVENTION

The invention relates to a viscometer for molten plastic.

BACKGROUND OF THE INVENTION

Such apparatuses are known, for example, in the laboratory field. Here the measurement channel is milled into a surface in an expensive manner. Cleaning of the milled notch is very expensive and complex. Furthermore, the milled passage may have only a limited cross-section. Differently dimensioned measurement channels require the use of a complete different viscometer.

DE 689 29 247 [U.S. Pat. No. 4,817,416] discloses a viscometer where the plastic melt is branched off from an extruder, guided to a measuring path driven by a pump, and pumped back into the extruder by a further pump. For this purpose the measurement channel is comprised of two blocks between which an exchangeable capillary plate is arranged. However, the measuring apparatus has a many parts and is constructed in a costly manner, and its operation is very elaborate with regard to switching the capillary plate.

OBJECT OF THE INVENTION

The object of the invention is to further improve the known viscometer such that it is comprised of as few parts as possible, can be used as universally as possible, is economical to operate and, in particular, the structure defining the measurement channel can be changed in an easy and simple manner.

SUMMARY OF THE INVENTION

These objects are attained according to the invention in that the viscometer for molten plastic is provided with a melt passage and a measurement channel that are formed between two flat parallel surfaces, between which an exchangeable planar channel-forming element forming the measurement channel by means of a slot, is arranged, both an outgoing conduit and a return conduit for the melt branching off the melt passage, openings for the measurement sensors end at the slot of the channel-forming element on at least one of the planar faces, the return conduit being shorter than the outgoing conduit, a pump being arranged only in the outgoing conduit.

Due to the fact that the apparatus has both a melt passage and the measurement channel, they may be as close as possible to each other so that the outgoing conduit and in particular the return conduit may be particularly short so any pressure losses may be kept very low and any pressure variations otherwise resulting from changes in viscosity may be maintained at a negligibly low rate. With this construction only one pump is required.

It is advantageous that the planar face is formed by a housing that is divided in two to both sides of the melt passage, the housing being split in the region of the parallel faces, the housing parts having the planar faces being joined by interconnection through the channel-forming element.

Due to the fact that the apparatus is in a housing, a very compact construction of the apparatus is possible, thus ensuring particularly good temperature control.

It has been well proven that the housing parts are connected to each other via a hinge, and are spaced from each other such that the channel-forming element may be positioned between the planar faces. By opening one of the sides of the two-part housing one housing part may be folded away from the other. The planar faces to be cleaned can be accessed easily, and the channel-forming element may be switched out in a simple manner.

It is worth noting that the housing is shaped as a round disk having an axially centrally throughgoing melt passage, that the housing is divided into two parts at a tangentially division, and that the channel-forming element is between the two housing parts. The best possible temperature control is ensured due to the round form.

Preferably, the exchangeable channel-forming element is a single-use metal foil. Contrary to the prior art as described above, after cleaning of the capillary plate, a simple exchange of foils produced inexpensively is thus provided, the cleaning of which would be too complicated, and would usually lead to measurement and sealing problems.

A particular advantage is that different metal foils may have slots comprising different widths. Due to the exchange of channel-forming elements having a slot of a certain width with a slot of a different width, various materials, even those having widely varying viscosities, may be processed by the apparatus according to the invention without any problems.

Another possibility of changing the cross-section of the measurement channel is the fact that different metal foils may have varying thicknesses. For this purpose the spacing of the planar faces can be adjusted to the thickness of the respective channel-forming elements.

It has been well proven that the channel-forming elements/metal foils have at least one centering formation interacting with at least one centering counter-piece in at least one of the housing parts. This ensures that the channel-forming element is optimally positioned between the two housing parts without any problems after exchange and installation.

Another advantage is the provision of heaters connected to at least the planar faces such that the melt transported through the measurement channel is not subject to any changes of viscosity by temperature fluctuations. This is also facilitated if a heater is connected to the channel-forming element.

If necessary, a seal may be provided in the housing parts between the channel-forming element and at least one of the two planar faces.

A universal use of the apparatus is ensured if the melt passage of the apparatus is arranged or clamped between the head piece of an extruder and the input of an injection mold.

BRIEF DESCRIPTION OF THE DRAWING

The invention is explained in further detail based on a drawing. Therein.

DETAILED DESCRIPTION

Figure 1:
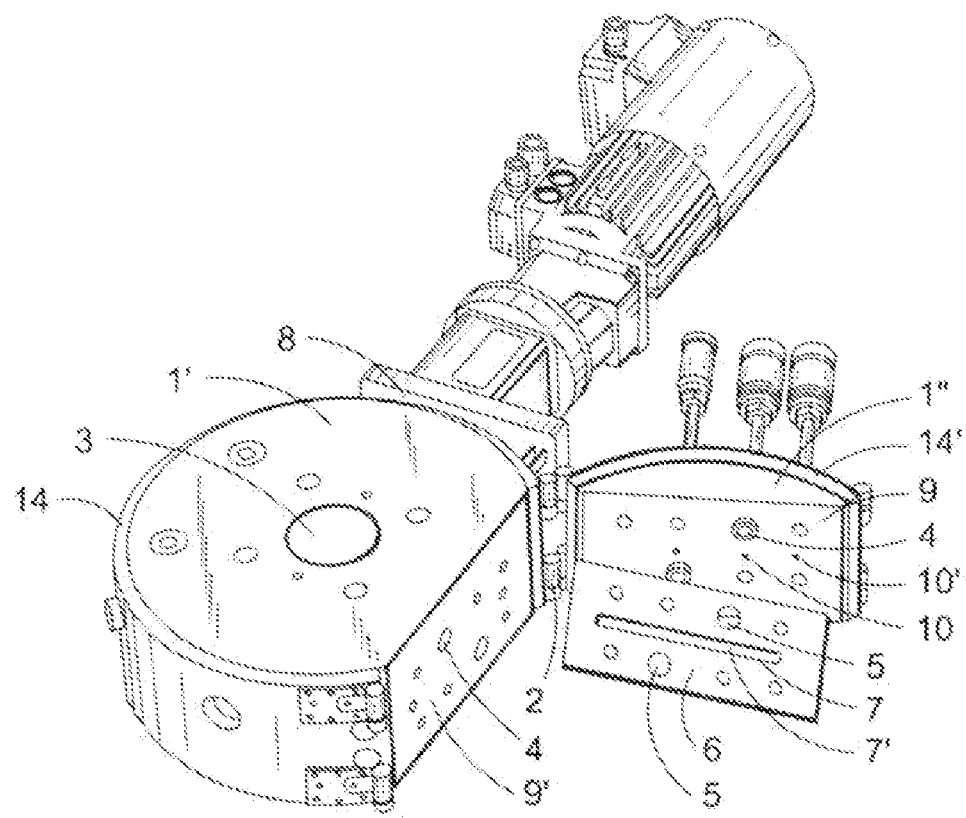
FIG. 1 shows the apparatus according to the invention in the open position.

FIG. 1 shows a housing 1 of the apparatus. The housing 1 is comprised of a housing part 1' and a housing part 1" connected to the housing part 1' via a hinge 2. The melt passage 3 can be seen in the housing part 1'. The housing part 1" has centering formations 4 that can fit with respective counter-centering formations 5 in the channel-forming element 6. Of course, the centering formations may also be on the channel-forming element 6, while the counter-centering formations are then on at least one of the housing parts 1' and 1". The channel-forming element 6 can therefore be placed in a centered position on the housing part 1". Part of a slot 7 in the channel-forming element 6 forms the measurement channel 7' in the closed position of the housing parts 1' and 1".

A pump 8 is provided on the housing part 1' for pumping melt drawn from the melt passage 3 through the measurement channel 7' at a predetermined pressure. Three sensors 13, 13' and 13" are arranged in the housing part 1" that open at a planar face 9 of the housing part 1" at respective positions 10, 10' and 10". The sensors 13 and 13' are, for example, pressure sensors. The viscosity is determined along the measurement channel 7' extending between the two pressure sensors, e.g. between the positions 10 and 10', via the pressure drop. The sensor 13" is, for example, a temperature sensor.

Figure 2:
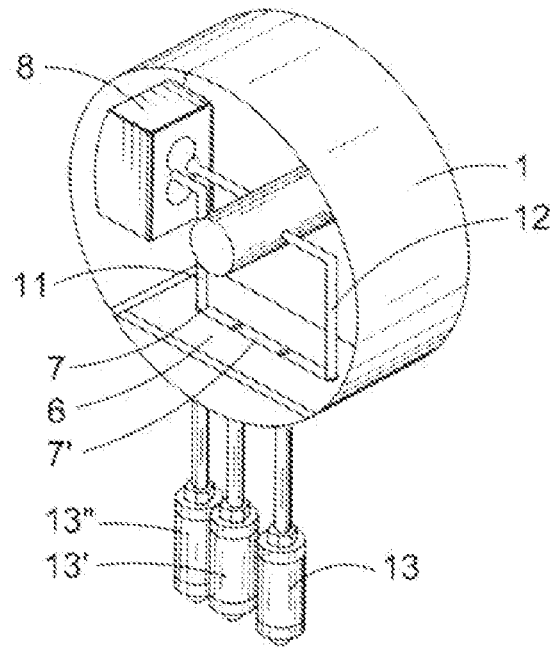
FIG. 2 a perspective, cross-sectional view of the apparatus according to the invention.

FIG. 2 shows the housing 1 with the melt passage 3, from which an outgoing conduit 11 and a return conduit 12 extend. The outgoing conduit 11 leads via the pump to the measurement channel 7' formed by the slot 7 in the channel-forming element 6.

To this end, the apparatus according to the invention functions as follows. Melt pumped from the melt passage 3 is preferably forced to flow into the measurement channel 7' by the pump 8 via the outgoing conduit 11 at a certain pressure. For example, the pressure drop of the melt may then be determined along the length of the measurement channel 7' via the sensors 13, 13' so that the viscosity of the melt can be calculated.

For this purpose the heaters 14 and 14', for example heating trays, ensure that the melt in the housing 1 does not cool down too much.

The invention claimed is:

1. A viscometer for molten plastic, the viscometer comprising:
   a housing forming a melt passage and having two parts with planar faces;
   a hinge connecting the parts together such that in a closed position the faces are parallel and closely juxtaposed;
   a single-use metal foil between the faces in the closed position and having a slot forming a measurement channel, the housing being formed with an outgoing conduit and a return conduit that branch off the melt passage for the melt and with openings for measurement sensors that end at the slot on at least one of the planar faces, the return conduit being shorter than the outgoing conduit, and
   a pump only in the outgoing conduit.

2. The apparatus according to claim 1 wherein the housing is shaped as a round disk and the melt passage is axially in a center thereof, that the housing is separated by a secantal division at the faces, and that the measurement channel is between the two housing parts.

3. The apparatus according to claim 1 wherein different metal foils have slots of varying width.

4. The apparatus according to claim 1 wherein different metal foils have various thicknesses.

5. The apparatus according to claim 1 wherein each metal foil has at least one centering formation that fits with counter-centering formation in at least one of the housing parts.

6. The apparatus according to claim 1 wherein heaters are connected to at least the planar faces.

7. The apparatus according to claim 1 wherein a heater is connected to the channel-forming element.

8. The apparatus according to claim 1, further comprising
   a seal is provided between the foil and at least one of the housing parts, or at least one of the planar faces.

9. The apparatus according to claim 1 wherein the melt passage of the apparatus is between a head piece of an extruder and an input of an injection mold.

10. A viscometer for molten plastic, the viscometer comprising:
    a housing having first and second relatively displaceable parts with generally complementary and substantially planar faces, the first part being formed with a through-going melt passage adapted for connection in a flow system of the molten plastic;
    a hinge interconnecting the parts;
    a pump on the first housing part having an intake and an output;
    an outgoing conduit extending from the melt passage to the pump intake and from the pump output to an opening on the face of the first housing part;
    a plurality of sensors on one of the parts connected to respective openings on the face of the one part;
    a return conduit shorter than the outgoing conduit and extending from another opening on the face of the first housing part offset from the opening of the outgoing line to the melt passage;
    an exchangeable metal foil formed with a slot into which all of the openings open is engaged tightly between the two faces; and
    means for latching the two parts together in a closed position with the metal foil held tightly between the two faces, whereby molten plastic drawn by the pump out of the melt passage through the outgoing passage is forced through a channel formed between the faces by the slot and passes thence through the return conduit back into the melt passage.

11. The viscometer defined in claim 10 wherein the sensors are located on the second part of the housing.

12. The viscometer defined in claim 10 wherein the two parts have a generally cylindrical shape centered on an axis in the closed position, the passage extending through the first part at the axis, the two faces extending secantally.

13. The viscometer defined in claim 10 wherein there are three such sensors including two pressure sensors and a temperature sensor.

14. The viscometer defined in claim 10, further comprising:
    complementary centering formations on at least one of the faces and on the metal foil for ensuring positioning of the metal foil with its slot aligned with the openings.

15. The viscometer defined in claim 10 wherein the metal foil is disposable.

16. The viscometer defined in claim 10, further comprising heating means for maintaining an elevated temperature of the faces and body.

* * * * *